United States Patent [19]

Watanabe

[11] Patent Number: 4,820,634

[45] Date of Patent: Apr. 11, 1989

[54] IMMUNOASSAY METHOD AND IMMUNOREACTIVE CELL REAGENT

[75] Inventor: Fumio Watanabe, Hachioji, Japan

[73] Assignee: Tokyo Shibaura Denki Kabushiki Kaisha, Kawasaki, Japan

[21] Appl. No.: 62,383

[22] Filed: Jun. 15, 1987

Related U.S. Application Data

[63] Continuation of Ser. No. 521,073, Aug. 8, 1983, abandoned.

[30] Foreign Application Priority Data

Aug. 11, 1982 [JP] Japan .................................. 57-139454
Nov. 5, 1982 [JP] Japan .................................. 57-195116
Nov. 5, 1982 [JP] Japan ...................................... 195117

[51] Int. Cl.$^4$ .............................................. G01N 33/53
[52] U.S. Cl. ............................................ 435/7; 435/15; 435/18; 435/25; 435/26; 435/177; 435/182; 436/520; 436/522; 436/821
[58] Field of Search ................... 435/7, 15, 18, 25, 26, 435/177, 182; 436/520, 522, 821

[56] References Cited

U.S. PATENT DOCUMENTS

| | | | |
|---|---|---|---|
| 3,843,777 | 10/1974 | Hainski et al. | 436/520 |
| 3,850,578 | 0/1974 | McConnell . | |
| 4,001,480 | 1/1977 | Shank | 435/182 |
| 4,130,634 | 12/1978 | Molinaro et al. | 436/520 |
| 4,483,921 | 11/1984 | Cole | 435/7 |
| 4,483,929 | 11/1984 | Szoka | 435/7 |
| 4,492,761 | 1/1985 | Durack | 436/519 |
| 4,619,903 | 10/1986 | Bartos et al. | 435/4 |

OTHER PUBLICATIONS

Weir, Handbook of Experimental Immunology in Three Volumes, vol. 1 Immunochemistry, Chapter 5B, pp. 5B.1-5B.2.

D'Orazio et al., "Ion Electrode Measurements of Complement and Antibody Levels...", Analytical Chemistry, vol. 49, No. 13, Nov. 1977, pp. 2083-2086.

Chemical Abstracts 78: 120694m.

*Primary Examiner*—Robert J. Warden
*Assistant Examiner*—Stephen Wieder
*Attorney, Agent, or Firm*—Cushman, Darby & Cushman

[57] ABSTRACT

Immunoassay which can be performed within a short period of time and a reagent composition for such immunoassay. The reagent composition contains complement and cells which contain quantitatively determinable substance therein. Antibody or antigen corresponding to antigen or antibody to be determined in a sample is bound on the outer surfaces of the cell membranes, which can be lysed by the complement upon activation thereof. In the immunoassay, a sample containing antigen or antibody to be determined is mixed with the reagent composition. The complement is activated by the resultant antigen-antibody complex. The cell membranes are lysed by the complex and the determinable substance in the cells is liberated from the cells. The amount of the liberated substance is determined.

9 Claims, 4 Drawing Sheets

IMMUNOASSAY METHOD AND IMMUNOREACTIVE CELL REAGENT

This is a continuation of application Ser. No. 521,073, filed Aug. 8, 1983 which was abandoned upon the filing hereof.

BACKGROUND OF THE INVENTION

1. Field of the Invention

The present invention relates to a reagent composition for use in immunoassay and immunoassay using the same.

2. Description of the Prior Art

As a conventional immunoassay, radioimmunoassay (RIA) is known in which a specific antigen (or antibody) in a sample from a biological organism is quantitatively determined utilizing the immunological reaction between antibody (or antigen) marked with radioisotope and the antigen (or antibody) in the sample. Enzyme immunoassay is also widely known in which antigen-antibody complex is obtained by the antigen-antibody reaction between antibody (or antigen) marked with enzyme and antigen (or antibody) in a sample from a biological organism. Specific antigen (or antibody) in the sample is determined utilizing the enzyme reaction of the marker enzyme.

However, both RIA and enzyme immunoassay are disadvantageous in that several hours to several tens of hours are required before a satisfactory detection sensitivity is obtained.

SUMMARY OF THE INVENTION

It is an object of the present invention to provide a reagent composition for immunoassay and immunoassay using the same, which is capable of determining an antigen or antibody in a sample within a short period of time.

The reagent composition for immunoassay according to the present invention contains cells whose cell membranes can be lysed by complement upon activation thereof. Antibody (or antigen) specifically directed to an antigen (or antibody) to be determined in a sample is bound or fixed on the outer surfaces of the cell membranes of the cells. The cells contain a substance which is quantitatively determinable. The reagent composition of the present invention further contains complement.

According to the immunoassay of the present invention, the reagent composition is mixed with a sample containing antigen (or antibody) to be determined. Antigen-antibody complex is formed by the antigen-antibody reaction between the antigen (or antibody) in the sample and the antibody (or antigen) fixed on the outer surfaces of the cell membranes of the cells. The complement in the reagent composition is activated by the antigen-antibody complex, and the cell membrane is lysed by the activated complement. As a result, the determinable substance in the cells is liberated from the cell. The amount of the substance liberated from the cell is then determined. When the amount of the antigen (or antibody) in the sample to be determined is great, the number of cells whose cell membranes are lysed is also great. Accordingly, when the total amount of the substance liberated from the cells is measured, the amount of antigen or antibody in the sample can be determined from this total measured amount.

The present invention also provides a reagent for immunoassay comprising cells whose cell membranes can be lysed by complement upon activation thereof, antibody fixed on outer surfaces of the cell membranes of the cells, the specific antigen of the fixed antibody being the cell membrane itself, and a quantitatively determinable substance contained in the cells.

The present invention also provides immunoassay using the reagent as described above. According to this immunoassay, sample containing antigen (or antibody) to be determined is mixed with antibody (or antigen) specifically binds the antigen (or antibody), and with complement. Then, antigen-antibody complex is produced by the antigen-antibody reaction, and a portion of the complement is consumed by being bound to the antigen-antibody complex. The resultant mixture is then mixed with the reagent described above. At the surface of the cells of the reagent, antibody corresponding to the cell membranes is prefixed to form antigen-antibody complex. Thus, the complement remaining in the mixture is activated by the antigen-antibody complex to lyse the cell membranes. As a result, the quantitatively determinable substance is liberated from the cells. Quantitative determination of the substance liberated from the cells allows quantitative determination of the antigen (or antibody) in the sample to be determined.

According to the present invention, immunoassay can be performed within a short period of time.

DETAILED DESCRIPTION OF THE PREFERRED EMBODIMENTS

Figure 1:
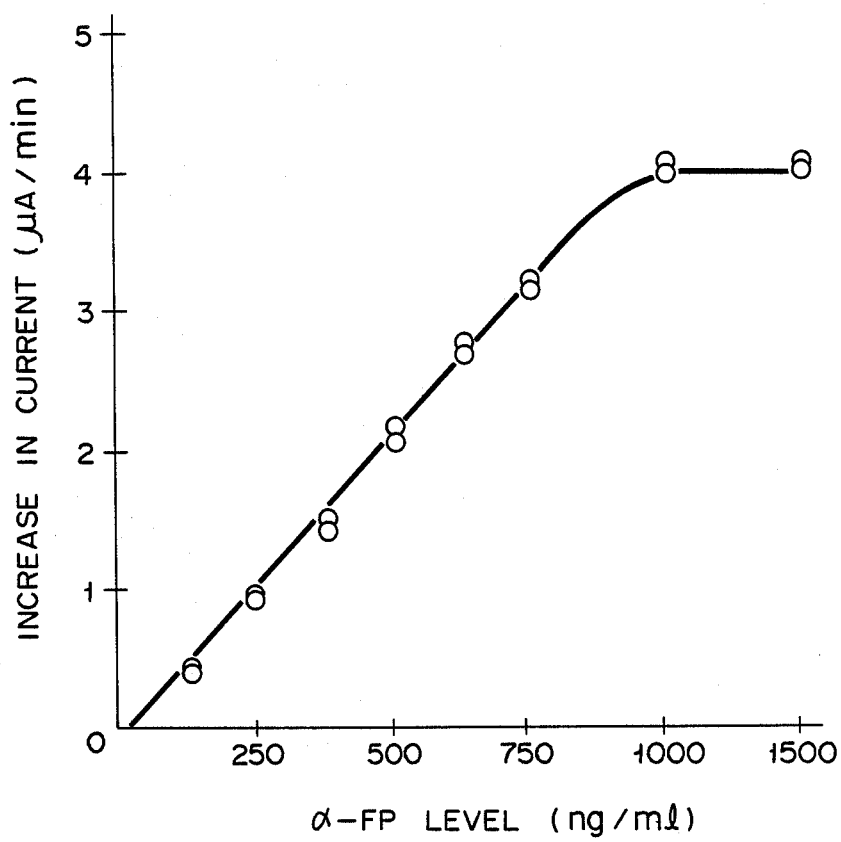
FIGS. 1, 3 and 5 are graphs showing calibration curves obtained according to the immunoassay of the present invention.

The reagent composition for immunoassay of the present invention contains, as a first component, cells having cell membranes which can be lysed by complement upon activation thereof. "Cells" to be used herein may be of any type whose cell membranes can be lysed by the activated complement, which can have antibody or antigen fixed on the outer surfaces of the cell membranes, and which can contain determinable substance. An example of such cells is red blood cells. A preferred type of red blood cell is sheep red blood cell since it has low selectivity of an antibody or antigen which can be fixed on the cell membrane. Another example of the cell which can be suitably used herein is sheep red blood cell ghost. Accordingly, the term "cell" used herein must be taken to include "cell ghost", except where it is apparent that it simply means cell.

Antibody (or antigen) which specifically binds with antigen (or antibody) to be determined in a sample is bound on the outer surfaces of cell membranes of the cells. Antigen or antibody to be determined may be arbitrarily selected. Examples of such antigen or antibody to be determined include α-fetoprotein (α-FP) contained in blood sample from a patient suffering from cancer, Hepatitis B surface antigen contained in blood sampled from a patient suffering from Hepatitis B, or antiepileptic for treatment of epilepsy. Antibody (or antigen) fixed on the outer surfaces of the cell membranes of cells must be one which specifically complexes with the antigen (or antibody) to be determined by the antigen-antibody reaction. For example, when antigen to be determined is antibody α-FP, an anti-α-FP antibody is fixed on the cell membranes.

The cells contain a quantitatively determinable substance. If the cells are red blood cells, this substance can be hemoglobin which is intrinsically contained in the cells. Hemoglobin can be determined by a color test.

If the cell is red blood cell ghost, the ghost can contain various types of determinable substance. A preferred example of such substance is enzyme. The amount of enzyme can be measured by determining the amount of enzyme reaction product with a substrate which the enzyme specifically catalyzes. If the quantitatively determinable substance contained in the cells is enzyme, the reagent composition must further contain a substrate which has specificity to the enzyme. Examples of such enzymes may include oxidases such as glucose oxidase, uricase, glycerol oxidase and cholesterol oxidase; dehydrogenases such as lactate dehydrogenase, glucose dehydrogenase and glutamate dehydrogenase; decarboxylases such as glutamate decarboxylase, urease and pyruvate decarboxylase; hydrolases such as aspartase, adenosine deaminase, nucleosidase, creatine amidinhydrase, alkaline phosphatase and acid phosphatase; transferases such as pyruvate kinase, creatine kinase and aspartate transaminase; isomerases such as glutamate racemase and alanine racemase; and mixtures thereof. Note that the cells may contain therein microorganisms containing such an enzyme.

It is also possible to seal inside the red blood cell ghosts a substrate which is specifically catalyzed by such an enzyme. In this case, the reagent composition must further contain an enzyme which has specificity to such a substrate. If cells containing enzyme are stored for a long period of time, the enzyme may be deactivated. Accordingly, it is preferred that the cells contain a substrate therein.

The amount of enzyme to be contained in a reagent composition for immunoassay of the present invention is excessive with respect to antigen or antibody in a sample to be examined irrespective of whether the enzyme is contained in the cells or is outside the cells. More specifically, such an excess amount of enzyme corresponds to enzyme activity of 100 U/ml or more, and more preferably 500 to 1,000 U/ml with respect to 1 ng/ml to 1 μg/ml of the antigen or antibody in the sample. The substrate can be contained in the reagent in an amount corresponding to that of the enzyme.

The quantitatively determinable substance contained in the cells may be ions or a radioactive substance in place of those enumerated above. Ions can be determined using an ion electrode, and radioactive substance can be determined using a scintillation counter.

Cells having an antibody bound on the outer surfaces of their cell membranes and which contain therein a quantitatively determinable substance can be prepared in the following manner. A case will be described wherein sheep red blood cells are used as cells, anti-α-fetoprotein antibody is used as antibody, and glucose oxidase is used as a quantitatively determinable substance.

First, α-fetoprotein is adminstered to an animal such as rabbit, goat, mouse, rat, or the like by subcutaneous injection. As a result, anti-α-fetoprotein antibody is produced in the body of the animal. After one week has elapsed from administration of α-fetoprotein, blood is sampled from the animal and serum is separated. The serum is an antiserum which contains anti-α-fetoprotein antibody. In order to improve specificity of the antigen-antibody reaction, the antiserum may be further purified by a conventional technique.

Meanwhile, blood is sampled from sheep, and red blood cells are collected from the sampled blood. The thus collected red blood cells are suspended in buffer solution (pH 7) containing 0.15M of NaCl.

Subsequently, the antiserum containing the anti-α-fetoprotein antibody is mixed with the suspension of the sheep red blood cells. Then, the anti-α-fetoprotein antibody is adsorbed on the cell membranes of the sheep red blood cells, so that isotonic solution suspending therein sheep red blood cells having the anti-α-fetoprotein antibody bound on the outer surfaces of their cell membranes is provided.

Glucose oxidase is added to the isotonic solution in the amount of 500 to 1,000 U/ml. The resultant solution is held in a tube which consists of semipermeable membrane and has one closed end. When the solution is subjected to dialysis treatment using hypertonic solution such as 1M NaCl aqueous solution and is then subjected to another dialysis treatment using isotonic solution, hemoglobin in the red blood cells are transferred outside the cells through small pores formed in the cell membranes due to the difference in osmotic pressure. In their place, glucose oxidase is introduced into the red blood cells, and the cell membranes are reformed.

The reagent composition for immunoassay according to the present invention further contains complement as a second component. The complement may be one which is generally contained in animal blood; guinea pig serum may be used as complement-containing solution. Accordingly, the reagent composition of the present invention can be obtained by, for example, mixing the cell suspension prepared in the manner as described above with guinea pig serum.

In the first step of an immunoassay according to the present invention, a sample such as blood sample taken from a patient is mixed with the reagent composition according to the present invention as described above. Then, antigen-antibody complex is produced between the antigen (or antibody) to be determined in the sample and the antibody (or antigen) fixed on the cell membranes. The complement in the composition is activated by the antigen-antibody complex. The cell membranes are then lysed by the activated complement, and the quantitatively determinable substance in the cells is liberated therefrom. If the reagent composition contains an enzyme, the enzyme should be contained in a sufficient amount with respect to the antigen (or antibody) which is to be determined. More specifically, the amount of enzyme may be such that an enzyme activity of the enzyme per 1 ng to 1 μg of the antigen (or antibody) to be determined is preferably 100 U/ml or more, and more preferably 500 to 1,000 U/ml. When enzyme is used in such a large amount, the immunoassay can be performed within an extremely short period of time. For example, an immunoassay which conventionally takes several tens of hours takes only about 5 to 10 minutes according to the present invention.

In the second step of the immunoassay of the present invention, the substance released from the cells in quantitatively determined. Quantitative determination of this substance can be performed by various methods depending upon the type of determinable substance contained in the cells. If hemoglobin, which is intrinsically contained in red blood cells, is used as the determinable substance, absorbancy of the suppernatant obtained by centrifugal separation of the mixture of the sample and the reagent composition is measured. This color test can be conveniently performed by an apparatus having a combination of a centrifuge and a spectrophotometer. If enzyme or substrate is sealed in the cells, the enzyme reaction product is determined. If the enzyme reaction product is ions such as $NAD^+$, it can be determined using an ion electrode. If the enzyme reaction product is hydrogen peroxide as in cases wherein gluocose oxidase is reacted with D-glucose or pyruvate oxidase is reacted with pyruvate, it can be determined by using a hydrogen peroxide electrode. Alternatively, the determination can be performed by reacting the enzyme reaction product with a suitable reagent to color the reaction system, the absorbancy of which is then examined. For example, peroxidase is reacted with hydrogen peroxide in the presence of 4-aminoantipyrine, and a spectrum analysis of the resultant quinone pigment is performed. If ions are sealed in the cells, they can be determined using an ion electrode. If radioactive substance is sealed in the cells, it can be determined using a scintillation counter.

When the antigen or antibody to be determined is contained in the sample in a large amount, the amount of the antigen-antibody complex increases and the number of cells whose cell membranes are lysed also increases. As a result, the amount of the substance which is liberated from the cells increases. Measurement of the amount of the substance which is thus liberated from the cells allow quantitative determination of the antigen or antibody in the sample which is to be determined. This may be performed in accordance with a calibration curve, a preparation method thereof is well-known to those skilled in the art. More specifically, a certain amount of a sample containing an antigen or antibody in a known concentration and a certain amount of the reagent composition of the present invention are mixed, and the amount of the determinable substance liberated from the cells is determined. This operation is repeated while changing the concentration of the antigen or antibody in the sample. A calibration curve is prepared by plotting the concentration of the antigen or antibody along the axis of abscissa and the amount of the determinable substance released from the cells along the axis of ordinate. The unknown concentration of the antigen or antibody in a sample can be determined by measuring the amount of the substance liberated from the cells, and obtaining from the calibration curve the concentration of the antigen or antibody in the sample, which corresponds to the measured value.

In the immunoassay described above, the reagent composition of the present invention is prepared in advance, and is then mixed with a sample. However, it is also possible to mix the cells on whose cell membranes an anitbody or an antigen is fixed and containing determinable substance, complement, and sample together at the time of the immunoassay. Enzyme (or substrate) liberated from the cells can also be determined by, after it is liberated from the cells, adding substrate (or enzyme) specifically interacts therewith and determining the enzyme reaction product.

According to another aspect of the present invention, there is also provided a reagent for an immunoassay, comprising cells whose cell membranes can be lysed by complement upon activation thereof, antibody which is bound on the outer surfaces of cell membranes of the cells and whose corresponding antigen is the cell membrane itself, and quantitatively determinable substance which is contained in the cells.

This reagent for immunoassay is different from the above-described first component of the reagent composition of the present invention only in that the specific antigen corresponding to the antibody bound on the cell membranes is the cell membrane itself. In all other respects, the reagent remains the same as the first component of the above-described reagent composition. Antibody specifically corresponding to the cell membranes of cells can be obtained by sensitizing an animal with such cells and collecting serum from this animal. If the quantitatively determinable substance contained in the cells of the reagent is enzyme (or substrate), this reagent further contains a substrate (or enzyme) which specifically interacts with the enzyme (or substrate).

The present invention further provides an immunoassay using the reagent as described above.

In the first step of this immunoassay, (1) a sample containing antigen or antibody to be determined, (2) the antibody or antigen that specifically complexes with the antigen or antibody in the sample, and (3) complement are mixed together. As a result, an antigen-antibody complex is produced by the antigen-antibody reaction, and the complement is fixed to the antigen-antibody complex, so that a portion of the complement is consumed. At this time, complement which is not bound to the antigen-antibody complex must exist. For this purpose, the complement must be added in an amount exceeding that which is fixed to the antigen-antibody complex.

The resultant mixture and the reagent as described above are then mixed together. In the cells of the reagent, an antibody specifically corresponding to the cell membranes is prefixed to the cell membranes to form an antigen-antibody complex. Therefore, the complement remaining in the mixture is activated by the antigen-antibody complex and the cell membranes are lysed. As a result, the quantitatively determinable substance contained in the cells is released from the cells.

The amount of the substance which is liberated from the cells is then determined. This determination can be performed in the same manner as described above.

The amount of the antigen or antibody in the sample can be determined from the amount of the substance liberated from the cells in accordance with a calibration curve which is separately prepared in advance in the manner as described above.

In this immunoassay, the same reagent can be used irrespective of the type of antigen or antibody to be determined. This is because the antibody fixed on the cell membranes does not correspond to an antigen to be determined but corresponds to the cell membrane itself. For this reason, in this immunoassay, antibody or antigen which is specifically directed to the antigen or antibody to be determined need not be fixed to the cell membranes for each immunoassay. Many antibodies for use in the immunoassay are commercially available. Accordingly, if this reagent is once prepared in a large amount, an immunoassay of an antigen or antibody of any type may be performed without preparing a separate reagent for each antigen or antibody to be determined, resulting in convenience.

EXAMPLE 1

One hundred microliters of glycogen-containing (5 mg/ml) sheep red blood cells (2% in gelatin-Veronal buffer; pH 7.4) sensitized with anti-α-fetoprotein antibody, 100 μl of normal human blood serum to which α-fetoprotein was added in the amount of 100 to 1,500 ng/ml, 500 μl of guinea pig blood serum (complement value $CH_{50}$: 2.5) diluted five times with the above-mentioned buffer, and 1 ml of gelatin-Veronal buffer (pH 7.5) containing glucoamylase (50 U/ml) and glucose oxidase (102 U/ml) were added to a reaction vessel. The reaction mixture was incubated at 37° C. for 30 minutes. The cell membranes of the red blood cells were lysed by the immunological reaction. The glycogen liberated from the cells was decomposed to glucose by glucoamylase. The glucose was then oxidized by glucose oxidase to produce gluconic acid and hydrogen peroxide. The produced hydrogen peroxide was measured by a polarographic hydrogen peroxide detection electrode. As a consequence, a calibration curve as shown in FIG. 1 was obtained.

Figure 2:
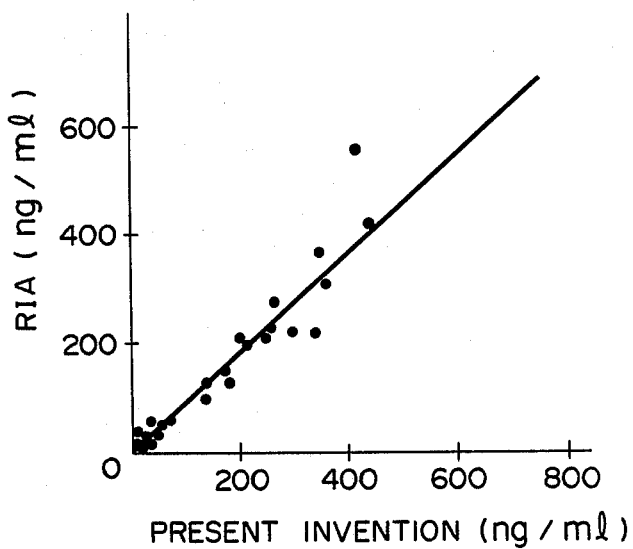
FIGS. 2, 4 and 6 are graphs in which the result obtained according to the immunoassay of the present invention is plotted along the axis of abscissa and that of the conventional RIA method is plotted along the axis of ordinate.

Using the same sample, the concentraion of the α-fetoprotein in the sample was measured by the conventional RIA method. In the graph shown in FIG. 2, the concentration obtained in Example 1 of the present invention is plotted along the axis of abscissa and that obtained by RIA is plotted along the axis of ordinate. It is seen from FIG. 2 that substantially the same results can be obtained by an immunoassay of the present invention and the established RIA method.

EXAMPLE 2

Figure 3:
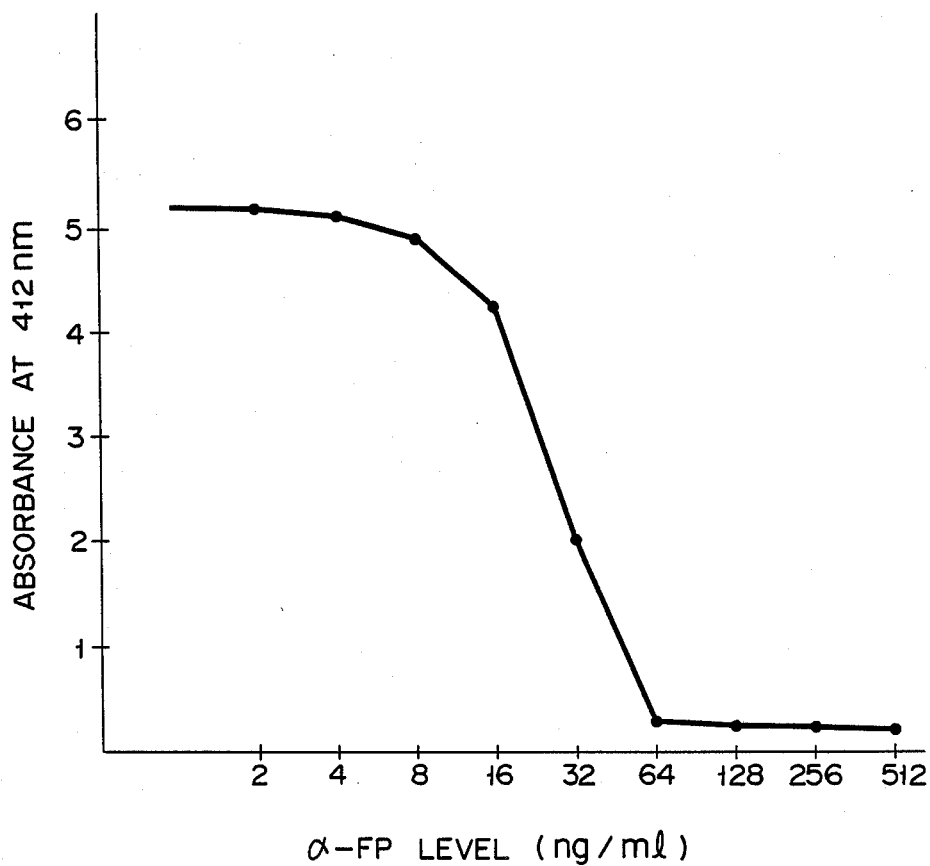

Two hundred microliters of an anti-α-fetoprotein antiserum diluted 100 times with a gelatin-Veronal buffer (pH 7.4), 200 μl of normal human blood serum to which α-fetoprotein was added in the amount of 2 to 512 ng/ml, and 500 μl of guinea pig blood serum (complement value $CH_{50}$: 2.5) diluted 100 times with the above-mentioned buffer were added to a reaction vessel in a spectrophotometer with a centrifuge. The reaction mixture was incubated at 37° C. for 30 minutes to consume a portion of the complement. Subsequently, 200 μl of sheep red blood cells (2% in the above-mentioned buffer) sensitized with anti-sheep red blood cell antibody, and 1 ml of the above-mentioned buffer were added to the reaction mixture. The resultant mixture was incubated at 37° C. for 30 minutes. Then, the centrifuge was rotated at 2,000 rpm and the absorbancy at a wavelength of 412 nm was measured. A calibration curve as shown in FIG. 3 was obtained.

Figure 4:
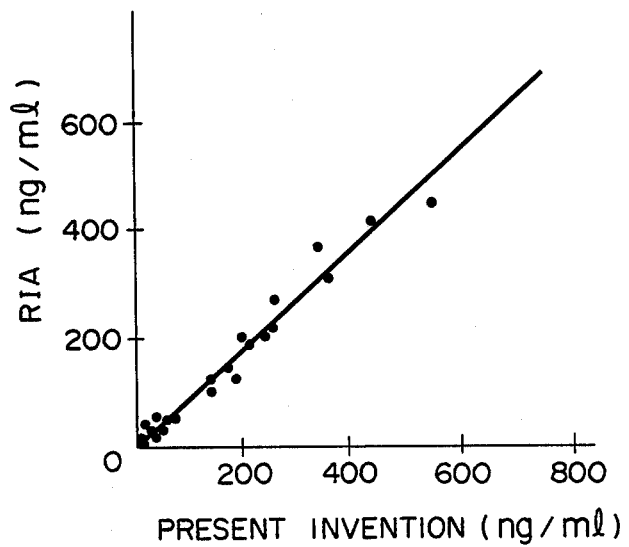

In the graph shown in FIG. 4, the concentration obtained in Example 2 is plotted along the axis of abscissa and that obtained by the conventional RIA is plotted along the axis of ordinate. It is seen from FIG. 4 that substantially the same results can be obtained by the method of Example 2 and the established RIA method.

EXAMPLE 3

Figure 5:
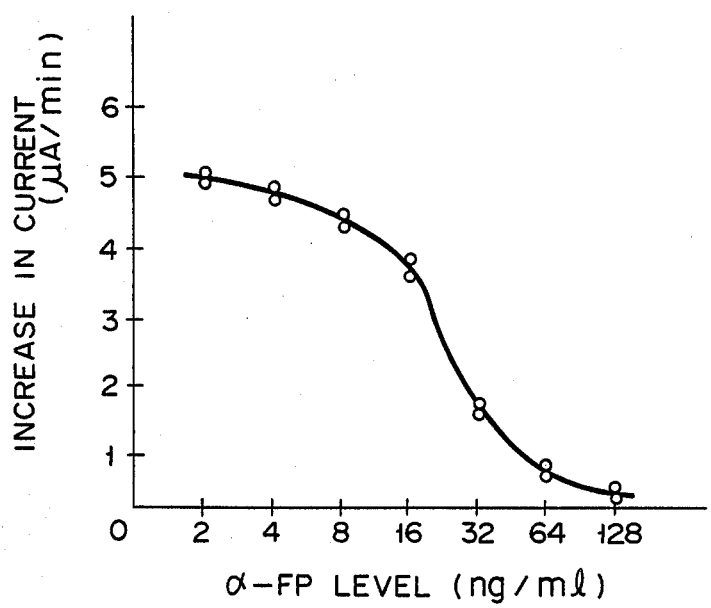

Two hundred microliters of an anti-α-fetoprotein antibody diluted 100 times with a gelatin-Veronal buffer (pH 7.4), 200 μl of normal human blood serum to which α-fetoprotein is added in the amount of 2 to 128 ng/ml, and 500 μl of guinea pig blood serum (complement value $CH_{50}$: 2.5) diluted 100 times with the above-mentioned buffer were added to a reaction vessel. The reaction mixture was incubated at 37° C. for 30 minutes to consume a portion of the complement. Two hundred microliters of glycogen-containing (5 mg/ml) sheep red blood cells sensitized with anti-sheep red blood cell antibody, and 1 ml of the above-mentioned buffer containing glycoamylase (50 U/ml) and glucose oxidase (102 U/ml) were added to the reaction mixture. The resultant mixture was incubated at 37° C. for 30 minutes. The cell membranes of the red blood cells were lysed by the remaining portion of the complement to liberate the glycogen from the cells. Hydrogen peroxide was produced by the action of the enzyme, which was measured by a polarographic hydrogen peroxide detection electrode. A calibration curve as shown in FIG. 5 was obtained.

Figure 6:
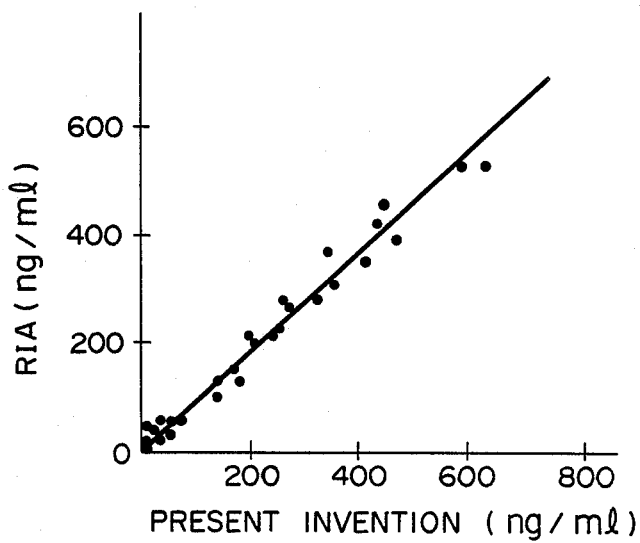

In the graph shown in FIG. 6, the concentration obtained in Example 3 of the present invention is plotted along the axis of abscissa, while that of the conventional RIA is plotted along the axis of ordinate. It is seen from FIG. 6 that substantially the same results can be obtained by the immunoassay of the present invention and the established RIA method.

What is claimed is:

1. An immunoassay method for quantitatively determining an antigen or antibody in a sample, the method comprising the steps of:

(1) mixing a sample containing complement and antigen or antibody to be quantitatively determined, together with an antibody or antigen which specifically interacts with the antigen or antibody to be determined to consume a portion of the complement;

(2) mixing a resultant mixture of step (1) with a reagent comprising (a) cells having cell membranes of a specific antigen, said cell membranes being capable of being lysed by complement upon activation thereof; (b) a specific antibody which is bound on outer surfaces of the cell membranes and which forms complex with the specific antigen of the cell membranes, and (c) quantitatively determinable substance contained in said cells, thereby lysing the cell membranes of said cells by a remaining portion of the complement and liberating the determinable substance from said cells; and (3) determining the amount of the determinable substance which was liberated from said cells as an indication of an amount of the antigen or antibody in the sample to be quantitatively determined.

2. The immunoassay according to claim 1, wherein said cells are red blood cells, and the determinable substance is hemoglobin, the determination of the amount of the hemoglobin liberated from said cells being performed by a color test.

3. A reagent composition for an immunoassay to quantitatively determine an antigen or antibody in a sample, said reagent composition comprising:

cells, whose cell membranes are capable of being lysed by a complement upon activation thereof after an immunospecific reaction, the cells having antibody whose corresponding antigen is the cell membrane itself being bound on the outer surfaces of the cell membranes and said cells containing an enzyme; and substrate that is specifically catalyzed by the enzyme.

4. The reagent composition according to claim 3, wherein the enzyme is a member selected from the group consisting of oxidase, dehydrogenase, decarboxylase, hydrolas, transferase, and isomerase.

5. The reagent according to claim 3, wherein said cells contain a microorganism therein, and the enzyme is contained in the microorganism.

6. A reagent composition for an immunoassay to quantitatively determine an antigen or antibody in a sample, said reagent composition comprising:

cells, whose cell membranes are capable of being lysed by a complement upon activation thereof after an immunospecific reaction, the cells having antibody whose corresponding antigen is the cell membrane itself being bound on outer surfaces of the cell membranes, and said cells containing substrate; and enzyme that specifically catalyzes the substrate.

7. The reagent composition according to claim 6, wherein the enzyme is a member selected from the group consisting of oxidase, dehydrogenase, decarboxylase, hydrolase, transferase, and isomerase.

8. An immunoassay method for quantititatively determining an antigen or antibody in a sample, the method comprising the steps of:

(1) mixing a sample containing antigen or antibody to be quantitatively determined, an antibody or antigen that specifically interacts with the antigen or antibody to be determined, and complement to consume a portion of the complement;

(2) mixing a resultant mixture, cells, the outer surfaces of cell membranes of which antibody whose corresponding antigen is the cell membrane itself is bound, the cells containing an enzyme, the cell membranes of which are capable of being lysed by a complement upon activation thereof, and substrate being specifically catalysed by the enzyme, thereby lysing said cells by a remaining portion of the complement and liberating the enzyme from said cells to cause an enzyme reaction with the substrate; and (3) determining the amount of an enzyme reaction product produced by the enzyme reaction as an indication of an amount of the antigen or antibody in the samples to be quantitatively determined.

9. An immunoassay method for quantitatively determining an antigen or antibody in a sample, the method comprising the steps of:

(1) mixing a sample containing antigen or antibody to be quantitatively determined, an antibody or antigen that specifically interacts with the antigen or antibody to be determined, and complement to consume a portion of the complement;

(2) mixing a resultant mixture, cells, the outer surfaces of cell membranes of which antibody whose corresponding antigen is the cell membrane itself being bound, the cells containing a substrate, the cell membrance of which are capable of being lysed by a complement by activation thereof, and an enzyme that specifically catalyzes the substrate, thereby lysing said cells by a remaining portion of the complement and liberating the substrate from said cells to cause an enzyme reaction with enzyme; and (3) determining the amount of an enzyme reaction product produced by the enzyme reaction as an indication of an amount of the antigen or antibody in the sample to be quantitatively determined.

* * * * *